US008024035B2

(12) United States Patent
Dobak, III (10) Patent No.: US 8,024,035 B2
(45) Date of Patent: Sep. 20, 2011

(54) ELECTRIC MODULATION OF SYMPATHETIC NERVOUS SYSTEM (75) Inventor: John D. Dobak, III, La Jolla, CA (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 1160 days.

(21) Appl. No.: 11/804,449

(22) Filed: May 17, 2007

(65) Prior Publication Data
US 2007/0225768 A1   Sep. 27, 2007

Related U.S. Application Data (62) Division of application No. 10/243,612, filed on Sep. 13, 2002, now Pat. No. 7,239,912.

(60) Provisional application No. 60/366,750, filed on Mar. 22, 2002, provisional application No. 60/370,311, filed on Apr. 5, 2002, provisional application No. 60/379,605, filed on May 10, 2002, provisional application No. 60/384,219, filed on May 30, 2002, provisional application No. 60/386,699, filed on Jun. 10, 2002.

(51) Int. Cl.
*A61N 1/372* (2006.01)
(52) U.S. Cl. ........................................... 607/2
(58) Field of Classification Search .......... 600/373, 600/377, 593; 607/2, 115, 116, 133, 118
See application file for complete search history.

(56) References Cited

U.S. PATENT DOCUMENTS

| 3,911,930 A | 10/1975 | Hagfors et al. |
| 4,315,509 A | 2/1982 | Smit |
| 4,501,264 A | 2/1985 | Rockey |
| 4,549,556 A | 10/1985 | Tarjan et al. |
| 4,573,481 A | 3/1986 | Bullara |
| 4,592,339 A | 6/1986 | Kuzmak et al. |
| 4,595,010 A | 6/1986 | Radke |
| 4,702,254 A | 10/1987 | Zabara |
| 4,827,935 A | 5/1989 | Geddes et al. |
| 4,867,164 A | 9/1989 | Zabara |

(Continued)

FOREIGN PATENT DOCUMENTS

JP   06165827 A2   6/1994

(Continued)

OTHER PUBLICATIONS

Ahren, B., Autonomic regulation of islet hormone secretion—Implications for health and disease, Diabetologia, 2000, 393-410, vol. 43.

(Continued)

*Primary Examiner* — Carl H Layno
*Assistant Examiner* — Frances Oropeza
(74) *Attorney, Agent, or Firm* — Craig Hoersten; Christopher S. L. Crawford; Melissa Acosta (57) ABSTRACT A method is described for the treatment of obesity or other disorders, by electrical activation or inhibition of the sympathetic nervous system. This activation or inhibition can be accomplished by electrically stimulating the greater splanchnic nerve or other portion of the sympathetic nervous system using an implantable pulse generator. This nerve activation can result in reduced food intake and increased energy expenditure. Reduced food intake may occur through a variety of mechanisms that reduce appetite and cause satiety. Increased adrenal gland hormone levels will result in increased energy expenditure. Fat and carbohydrate metabolism, which are also increased by sympathetic nerve activation, will accompany the increased energy expenditure.

2 Claims, 8 Drawing Sheets

U.S. PATENT DOCUMENTS

| | | | |
|---|---|---|---|
| 5,095,905 A | 3/1992 | Klepinski | |
| 5,107,833 A | 4/1992 | Barsness | |
| 5,121,754 A | 6/1992 | Mullett | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,281,581 A | 1/1994 | Cooper et al. | |
| 5,299,569 A | 4/1994 | Wernicke et al. | |
| 5,304,206 A | 4/1994 | Baker, Jr. et al. | |
| 5,306,300 A | 4/1994 | Berry | |
| 5,330,507 A | 7/1994 | Schwartz | |
| 5,330,515 A | 7/1994 | Rutecki et al. | |
| 5,335,657 A | 8/1994 | Terry, Jr. et al. | |
| 5,351,394 A | 10/1994 | Weinberg | |
| 5,423,872 A | 6/1995 | Cigaina | |
| 5,454,840 A | 10/1995 | Krakovsky et al. | |
| 5,458,626 A | 10/1995 | Krause | |
| 5,515,848 A | 5/1996 | Corbett, III et al. | |
| 5,531,778 A | 7/1996 | Maschino et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,690,691 A | 11/1997 | Chen et al. | |
| 5,707,400 A | 1/1998 | Terry, Jr. et al. | |
| 5,716,392 A | 2/1998 | Bourgeois et al. | |
| 5,725,563 A | 3/1998 | Klotz | |
| 5,755,750 A | 5/1998 | Petruska et al. | |
| 5,782,798 A | 7/1998 | Rise | |
| 5,820,584 A | 10/1998 | Crabb | |
| 5,836,994 A | 11/1998 | Bourgeois | |
| 5,861,014 A | 1/1999 | Familoni | |
| 5,866,547 A | 2/1999 | Flier et al. | |
| 5,868,141 A | 2/1999 | Ellias | |
| 5,919,216 A | 7/1999 | Houben et al. | |
| 5,922,015 A | 7/1999 | Schaldach | |
| 5,928,272 A | 7/1999 | Adkins et al. | |
| 5,995,872 A | 11/1999 | Bourgeois | |
| 6,026,326 A | 2/2000 | Bardy | |
| 6,041,258 A | 3/2000 | Cigaina | |
| 6,058,331 A * | 5/2000 | King | 607/62 |
| 6,068,596 A | 5/2000 | Weth et al. | |
| 6,097,984 A | 8/2000 | Douglas | |
| 6,109,269 A | 8/2000 | Rise et al. | |
| 6,129,685 A | 10/2000 | Howard, III | |
| 6,146,391 A | 11/2000 | Cigaina | |
| 6,146,416 A | 11/2000 | Andersen et al. | |
| 6,165,180 A | 12/2000 | Cigaina | |
| 6,169,924 B1 | 1/2001 | Meloy et al. | |
| 6,243,607 B1 | 6/2001 | Mintchev et al. | |
| 6,308,105 B1 | 10/2001 | Duysens et al. | |
| 6,321,124 B1 | 11/2001 | Cigaina | |
| 6,350,455 B1 | 2/2002 | Donovan | |
| 6,356,786 B1 | 3/2002 | Rezai et al. | |
| 6,356,787 B1 | 3/2002 | Rezai et al. | |
| 6,381,495 B1 | 4/2002 | Jenkins | |
| 6,438,423 B1 | 8/2002 | Rezai et al. | |
| 6,497,718 B1 | 12/2002 | Dewan | |
| 6,535,764 B2 | 3/2003 | Imran et al. | |
| 6,542,776 B1 | 4/2003 | Gordon et al. | |
| 6,558,320 B1 | 5/2003 | Causey et al. | |
| 6,572,627 B2 | 6/2003 | Gabbay | |
| 6,587,719 B1 | 7/2003 | Barrett et al. | |
| 6,600,954 B2 | 7/2003 | Cohen et al. | |
| 6,675,809 B2 | 1/2004 | Stack et al. | |
| 6,721,603 B2 | 4/2004 | Zabara et al. | |
| 6,758,219 B2 | 7/2004 | Sapala et al. | |
| 6,879,859 B1 | 4/2005 | Boveja | |
| 6,885,888 B2 | 4/2005 | Rezai | |
| 6,912,419 B2 | 6/2005 | Hill et al. | |
| 6,922,590 B1 | 7/2005 | Whitehurst | |
| 7,076,292 B2 | 7/2006 | Forsberg | |
| 7,149,574 B2 | 12/2006 | Yun et al. | |
| 7,155,278 B2 | 12/2006 | King et al. | |
| 7,236,822 B2 | 6/2007 | Dobak, III | |
| 7,239,912 B2 | 7/2007 | Dobak, III | |
| 7,433,734 B2 | 10/2008 | King | |
| 7,483,746 B2 | 1/2009 | Lee et al. | |
| 7,529,582 B1 * | 5/2009 | DiLorenzo | 607/2 |
| 7,551,964 B2 | 6/2009 | Dobak, III | |
| 7,771,382 B2 | 8/2010 | Levine et al. | |
| 2001/0014815 A1 | 8/2001 | Matsumura et al. | |
| 2002/0032177 A1 | 3/2002 | Allan et al. | |
| 2002/0065217 A1 | 5/2002 | Qian et al. | |
| 2002/0072780 A1 | 6/2002 | Foley | |
| 2002/0077675 A1 | 6/2002 | Greenstein | |
| 2002/0099419 A1 | 7/2002 | Cohen et al. | |
| 2003/0008838 A1 | 1/2003 | Havel et al. | |
| 2003/0014127 A1 | 1/2003 | Talja et al. | |
| 2003/0018367 A1 | 1/2003 | DiLorenzo | |
| 2003/0045909 A1 | 3/2003 | Gross et al. | |
| 2003/0144708 A1 | 7/2003 | Starkebaum | |
| 2003/0181958 A1 | 9/2003 | Dobak, III | |
| 2003/0191476 A1 | 10/2003 | Smit | |
| 2003/0211967 A1 * | 11/2003 | Bryant et al. | 514/2 |
| 2004/0015201 A1 | 1/2004 | Greenstein | |
| 2004/0039452 A1 | 2/2004 | Bessler | |
| 2004/0049209 A1 | 3/2004 | Benchetrit | |
| 2004/0089313 A1 | 5/2004 | Utley et al. | |
| 2004/0097989 A1 | 5/2004 | Molina Tigueros | |
| 2004/0107004 A1 | 6/2004 | Levine et al. | |
| 2004/0230255 A1 | 11/2004 | Dobak, III | |
| 2004/0249362 A1 | 12/2004 | Levine et al. | |
| 2004/0249416 A1 | 12/2004 | Yun et al. | |
| 2005/0065575 A1 | 3/2005 | Dobak | |
| 2005/0080395 A1 | 4/2005 | Levine et al. | |
| 2005/0080491 A1 | 4/2005 | Levine et al. | |
| 2005/0125020 A1 | 6/2005 | Meade et al. | |
| 2005/0143788 A1 | 6/2005 | Yun et al. | |
| 2005/0149146 A1 | 7/2005 | Boveja et al. | |
| 2005/0192614 A1 | 9/2005 | Binmoeller | |
| 2006/0178691 A1 | 8/2006 | Binmoeller | |
| 2007/0162085 A1 | 7/2007 | DiLorenzo | |
| 2008/0262411 A1 | 10/2008 | Dobak | |
| 2009/0259279 A1 | 10/2009 | Dobak | |
| 2010/0216709 A1 | 8/2010 | Scheule et al. | |

FOREIGN PATENT DOCUMENTS

| | | |
|---|---|---|
| JP | 09511421 T2 | 11/1997 |
| JP | 2004502506 T2 | 1/2004 |
| JP | 2004522526 T2 | 7/2004 |
| WO | 95/26783 A1 | 10/1995 |
| WO | 98/53878 A1 | 12/1998 |
| WO | WO 98/57701 | 12/1998 |
| WO | WO 00/61223 | 10/2000 |
| WO | WO 01/52932 | 7/2001 |
| WO | WO 01/58520 | 8/2001 |
| WO | WO 01/83028 | 11/2001 |
| WO | WO 02/04068 | 1/2002 |
| WO | WO 02/26315 | 4/2002 |
| WO | WO 02/26317 | 4/2002 |
| WO | WO 02/34331 | 5/2002 |
| WO | WO 02/43467 | 6/2002 |
| WO | WO 02/062291 | 8/2002 |
| WO | WO 03/086246 | 10/2003 |
| WO | WO 03/094785 | 11/2003 |
| WO | WO 2004/019765 | 3/2004 |
| WO | WO 2004/049982 | 6/2004 |
| WO | WO 2004/064680 | 8/2004 |
| WO | WO 2004/064685 | 8/2004 |
| WO | WO 2006/007048 | 1/2006 |
| WO | 2006/023498 A1 | 3/2006 |
| WO | 2004/075974 A3 | 4/2006 |
| WO | 2007/087332 A2 | 8/2007 |
| WO | 2007/146287 A3 | 4/2009 |

OTHER PUBLICATIONS

Ahren, B., Sympathetic Nerve Stimulation Versus Pancreatic Norepinephrine Infusion in the Dog: 1)Effects on Basal Release of Insulin and Glucagon; Endocrinology, Mar. 1986; pp. 323-331; vol. 121, No. 1.
Alamo, L..., Electrically-Evoked Catecholamine Release from Cat Adrenals; Biochemical Pharmacology, Nov. 1990, 973-978, vol. 42, No. 5.
Alvarez, et al., Sympathetic Neural Activation in Visceral Obesity, Circulation, Nov. 12, 2002, pp. 2533-2536.
Amar, A., Vagus Nerve Stimulation for Intractable Epilepsy, Cyberonics Brochure, Pub. Date unknown, thirteen pages.
Andrews, Russell J., Neuromodulation I. Techniques—Deep Brain Stimulation, Vagus Nerve Stimulation, and Transcranial Magnetic Stimulation, Ann. N. Y. Acad. Sci., 2003, 1-13, vol. 993.
Ballard, K. et al., The Unresponsiveness of Lipid Metabolism in Canine Mesenteric Adipose Tissue to Biogenic Amines and to Sympathetic Nerve Stimulation, Acta Physiol. Scan. 1969, 442-448, vol. 77.
Barone, Frank C., et al., Gastric Distension Modulates Hypthalamic Neurons Via a Sympathetic Afferent Path Through the Mesencephalic Periaqueductal Gray, Brain Research Bulletin, 1995, 239-251, vol. 38, No. 3.
Birks, R.I., Regulation by Patterned Preganglionic Neural Activity of Transmitter Stores in a Sympathetic Ganglion, J. Physiol., 1978, 559-572, vol. 280.
Blackshaw, L. A., et al., Vagal and sympathetic influences on the ferret lower oesophageal sphincter, *Journal of the Autonomic Nervous System*, 1997, 179-188, vol. 66.
Bloom, S., The Andrenal Contribution to the Neuroendocrine Responses to Splanchnic Nerve Stimulation in Conscious Calves, Journal of Physiology, Jul. 1987, 513-526, vol. 397.
Bray, Reciprocal relation of food intake and sympathetic activity: experimental observations and clinical implications, International Journal of Obesity, 2000, pp. S8-S17, 24, Suppl. 2.
Brown, et al., Changes in Food Intake with Electrical Stimulation of the Ventromedial Hypothalamus in Dogs, J Neurosurg, Jun. 1984, pp. 1253-1257, vol. 60.
Buckley, N., Circulatory Effects of Splanchnic Nerve Stimulation in Developing Swine; American Journal of Physiology, Apr. 1984, pp. H69-H74, vol. 248.
Bugbee, Martin, et al., Webpage, 1996, Design of a Selective Nerve Stimulator.
Cigaina, et al., Gastric Peristalsis Control by Mono Situ Electrical Stimulation: a Preliminary Study, Obesity Surgery, 1996, 247-249, vol. 6.
Cigaina, V., Long-Term Effects of Gastric Pacing to Reduce Feed Intake in Swine, Obesity Surgery, 1996, 250-253, vol. 6.
Clutter, W., Epinephrine Plasma Metabolic Clearance Rates and Physiologic Thresholds for Metabolic and Hemodynamic Actions in Man, Journal of Clinical Investigation, Jan. 1980, pp. 94-101, vol. 66.
Crago, et al., The Choice of Pulse Duration for Chronic Electrical Stimulation via Surface, Never, and Intramuscular Electrodes, Annals of Biomedical Engineering, 1974, 252-264, vol. 2.
Cummings, D., Plasma Ghrelin Levels after Diet-Induced Weight Loss r Gastric Bypass Surgery; The New England Journal of Medicine, May 2002, 1623-1630, vol. 346, No. 21.
Cuschieri, A., Bilateral Endoscopic Splanchnicectomy through a Posterior Thoracoscopic Approach; J.R. Coll. Surg. Edinb., Feb. 1994, 44-47, vol. 39.
Delbro, D., et al., Non-ganglionic cholinergic excitatory pathways in the sympathetic supply to the feline stomach, *Acta Physiol Scand.*, 1980, 137-144, vol. 110.
Deloof, S., Sympathetic control of antral and pyloric electrical activity in the rabbit, *Journal of the Autonomic Nervous System*, 1988, 1-10, vol. 22.
Dodt, C., et al., Sympathetic control of white adipose tissue in lean and obese humans, *Acta Physiol. Scand.*, 2003, 351-357, vol. 177.
Dodt, Christoph, et al., Intraneural stimulation elicits an increase in subcutaneous interstitial glycerol levels in humans, *Journal of Physiology*, 1999, 545-552, vol. 521.2.
Dodt, Christoph, et al., The Subcutaneous Lipolytic Response to Regional Neural Stimulation is Reduced in Obese Women, *Diabetes*, Nov. 2000, 1875-1879, vol. 49:1.
Dunning, et al., Pancreatic and Extrapancreatic Galanin Release During Sympathetic Neural Activiation, Am J Physiol Endocrinol Metab, Mar. 1990, 436-444, vol. 258.
Edwards, A., Adrenal Catecholamine Output in Response to Stimulation of the Splanchnic Nerve in Bursts in the Conscious Calf, Journal of Physiology, Sep. 1981, 409-419, vol. 327.
Edwards, A., Adrenal Medullary Responses to Stimulation of the Splanchnic Nerve in the Conscious Calf; Journal of Physiology, Jan. 1980, 15-27, vol. 308.
Edwards, A., The Effect of Splanchnic Nerve Stimulation on Adrenocortical Activity in Conscious Calves; Journal of Physiology, Apr. 1986, 385-396, vol. 382.
Edwards, A., The Glycogenolytic Response to Stimulation of the Splanchnic Nerves in Adrenalectomized Calves, Sheep, Dogs, Cats, and Pigs, Journal of Physiology, Nov. 1970, 741-759, vol. 213.
Edwards, A., The Sensitivity of the Hepatic Gylcogenolytic Mechanism to Stimulation of the Splanchnic Nerves, J. Physiol., 1972, 315-334, vol. 220.
Edwards, et al., The Effect of Splanchnic Nerve Stimulation on the Uptake of Atrial Natriuretic Peptide by the Adrenal Gland in Conscious Calves, J. Endocrinol. Invest., 1990, 887-892, vol. 13.
Engeland, W., Splanchnic Nerve Stimulation Modulates Steroid Secretion in Hypophysectomized Dogs; Neuroendocrinology, Agu. 1988, 124-131, vol. 50.
Fang, Zi-Ping, et al., Alternate excitation of large and small axons with different stimulation waveforms: an application to muscle activation, *Med. & Bio. Eng. & Comput.*, 1991, 543-547, vol. 29.
Fredholm, B. B., et al., Effects of Vasoactive Drugs on Circulation in Canine Subcutaneous Adiopose Tissue, Acta Physiol. Scand., 1970, 564-574, vol. 79.
Friesen , et al., Canadian Journal of Physiology and Pharmacology, The National Research Council of Canada, vol. 49, May 1971, No. 5, pp. 375-381.
Fukushima, K., et al., Differential Blocking of Motor Fibers by Direct Current, *Pflügers Arch.*, 1975, 235-242, vol. 358.
Furness, J., Effects of Vagal and Splanchnic Section on Food Intake, Weight, Serum Leptin, and Hypothalamic Neuropeptide Y in Rat, Autonomic Neuroscience: Basic and Clinical, Feb. 2001; pp. 28-36; vol. 92.
Hammond, et al., Vagus Nerve Stimulation in Humans: Neurophysiological Studies and Electrophysiological Monitoring, Epilepsia, 1990, pp. S51-S59, vol. 31, Suppl. 2.
Heck, et al., Vagus Nerve Stimulation Therapy, Epilepsy, and Device Parameters, Neurology 59, Suppl 4, Sep. 2002, pp. S31-S37.
Holst, et al. Nervous Control of Pancreatic Exocrine Secretion in Pigs, Acta Physiol. Scand., 1979, 33-51, vol. 105.
Hopp, F.A., et al., Effect of anodal blockade of myelinated fibers on vagal C-fiber afferents, *The American Physiological Society*, 1980.
Itina, L.V., et al., Impulsation of the splanchnic and vagus nerves after introduction of fat into the lumen of the small intestine, Sechnov Physiological Journal of the USSR, Institute of Physiology Acad. Sci. BSSR, Minsk, 1972 (Russian text with English abstract).
Itina, L.V., Sympatho-activatory and sympatho-inhibitory afferent fibers of vagus and splanchnic nerves, Sechenov Physiological Journal of the USSR, Institute of Physiology Acad. Sci. Belorus. SSR, Minsk, 1979 (Russian text with English abstract).
Ito, Shigeo, et al., Gastric Vasodilator and Motor Responses to Splanchnic Stimulation and Tachykinins in the Dog, *Gen. Pharmac*, 1993, 291-298, vol. 24, No. 2.
Jarhult, M.D., et al., The Functional Importance of Sympathetic Nerves to the Liver and Endocrine Pancreas, Ann. Surg., Jan. 1979, 96-100, vol. 189, No. 1.
Jaw, F.-S, et al., A modified "triangular pulse" stimulator for C-fibers stimulation, *Journal of Neuroscience Methods*, 1991, 169-172, vol. 37.
Jonson, et al., Splanchnic Nerve Stimulation Inhibits Duodenal HCO3 Secretion in the Rat, American Physiological Society, 1988, pp. G709-G712.
Jorum, et al., Analgesia by low-frequency nerve stimulation mediated by low-threshold afferents in rats, Pain, 1988, 357-366, vol. 32.

Kaneto, A., et al., *Effect of splanchnic nerve stimulation on glucagons and insulin output in the dog*, Endocrinolgy, Jan. 1975, 96(1): 143-50.

Katzeff, H., Metabolic Studies in Human Obesity during Overnutrition and Undernutrition: Thermogenic and Hormonal Responses to Norepinephrine, Metabolism; Feb. 1986; 166-175; vol. 35, No. 2.

Koo, et al., Human Vagus Nerve Electrophysiology, J Clin Neurophysiol, Sep. 2001, 18(5), pp. 429-433.

Kuo, D., A Wide Field Electron Microscope Analysis of the Fiber Constituents of the Major Splanchnic Nerve in Cat, The Journal of Comparative Neurology, Apr. 1982, pp. 49-58, vol. 210.

Kurose, T. et al., Gulcagon, insulin and somatostatin secretion in response to sympathetic neuralactivation in streptozotocin-induced diabetic rats: a study with the isolatedperfused rat pancreas in vitro, Diabetologia, Nov. 1992, 1035-41, 35(11).

Kurose, T., Mechanism of Sympathetic Neural Regulation of Insulin, Somatostatin, and Glucagon Secretion; American Journal of Physiology, Mar. 1989, pp. E220-E227; vol. 258.

Leibel, R., Changes in Energy Expenditure Resulting from Altered Body Weight, The New England Journal of Medicine, Mar. 1995, 621-628, vol. 332, No. 10.

Lerman, M.D., Sheldon H., et al., Gastric Motor Response to Sympathetic Nerve Stimulation, Journal of Surgical Research, 1982, 15-23, vol. 32.

Lerman, M.D., Sheldon H., et al., Pyloric motor response to sympathetic nerve stimulation in dogs, *Surgery*, 1981, 460-465, vol. 89, No. 4.

Lockard, et al., Feasibility and Safety of Vagal Stimulation in Monkey Model, Epilepsia, 1990, pp. S20-S26, vol. 31, Suppl. 2.

Matthews, D., Effect of Epinephrine on Amino Acid and Energy Metabolism in Humans; American Journal of Physiology, Sep. 1989, pp. E948-E956, vol. 258.

Mirkin, B., Factors Influencing the Selective Secretion of Adrenal Medullary Hormones, Journal Pharmacol. Exp. Ther., Oct. 1960, pp. 218-225, vol. 132.

Mokdad, A., The Continuing Epidemics of Obesity and Diabetes in the United States; Journal of the American Medical Association, Sep. 2001, pp. 1195-1200, vol. 286, No. 10.

Monroe, Mary Beth, et al., Direct Evidence for Tonic Sympathetic Support of Resting Metabolic Rate in Healthy Adult Humans, Am. J. Physiol Endocrinol Metab., 2001, pp. E740-E744, vol. 280.

Naidoo, N., *Thoracic Splanchnic Nerves: Implications for Splanchnic Denervation*, Journal of Anatomy, Jun. 2001, pp. 585-590. vol. 199.

Nakazato, Yoshikazu, et al., Atropine- and hexamethonium-resistant motor response to greater splanchnic nerve stimulation in the dog stomach, *Journal of the Autonomic Nervous System*, 1987, 35-42, vol. 20.

Nakazato, Yoshikazu, et al., Gastric Motor and Inhibitor Response to Stimulation of the Sympathetic Nerve in the Dog, *Jap. J. Pharmac*, 1970, 20: 131-141.

Opsahl, Charles A., Sympathetic nervous system involvement in the lateral hypothalamic lesion syndrome, *Department of Psychology*, Yale University, New Haven Connecticut 06520, Jul. 7, 1976.

Oro, Lars, et al., Influence of Electrical Supramedullary Stimulation on the Plasma Level of Free Fatty Acids, Blood Pressure and Heart Rate in the Dog, *Acta Medica Scandinavica*, 1965, 697-711, vol. 178.

Pan, et al., Role of Summation of Afferent Input in Cardiovascular Reflexes from Splanchnic Nerve Stimulation, The American Physiological Society, 1996, pp. H849-H856.

Peterson, H., Body Fat and the Activity of the Autonomic Nervous System; The New England Journal of Medicine, Apr. 1988, 1078-1083, vol. 318, No. 17.

Ratheiser, K., Epinephrine Produces a Prolonged Elevation in Metabolic Rate in Humans, American Journal of Nutrition, Oct. 1997, 1046-1052, vol. 68.

Ravussin, E., Reduced Rate of Energy Expenditure as a Risk Factor for Body-Weight Gain, The New England Journal of Medicine, Feb. 1998, 467-472, vol. 318, No. 8.

Rosell, Sune, Release of Free Fatty Acids from Subcutaneous Adipose Tissue in Dogs Following Sympathetic Nerve Stimulation, *Acta Physiol. Scand.*, 1966, 67:343-351.

Rozman, et al., Multielectrode Spiral Cuff for Selective Stimulation of Nerve Fibres, Journal of Medical Engineering & Technology, Sep./Oct .1992, pp. 194-203, vol. 16, No. 5.

Rozman, J., et al., Recording of ENGs from the nerves innervating the pancreas of a dog during the intravenous glucose tolerance test, National Library of Medicine, Physiol Meas., Nov. 2002, 695-705, 23(4).

Rozman, Janez, et al., Recording of electroneurograms from the nerves innervating the pancreas of a dog, *Journal of Neuroscience Methods*, 2001, 112:155-162.

Rozman, Janez, et al., Stimulation of Nerves Innervating the Dog's Pancreas, *Artificial Organs*, 2002, 26(3):241-243.

Shimazu, T., Central Nervous System Regulation of Liver and Adipose Tissue Metabolism, *Diabetologia*, 1981, 343-356, vol. 20.

Sjostrom, L., Epinephrine Sensitivity with respect to Metabolic Rate and Other Variables in Women, American Journal of Physiology, Sep. 1982, pp. E431-E442, vol. 245.

Staten, M., Physiolotical Increments in Epinephrine Stimulate Metabolic Rate in Humans, American Journal of Physiology, Nov. 1986, pp. E322-E220, vol. 253.

Stoddard, et al., Adrenal Medullary Secretion with Splanchnic Stimulation in Spinal Cats, Journal of the Autonomic Nervous System, 1992, 105-116, vol. 38.

Strickland, T., Performance of Local Anesthetic and Placebo Splanchnic Blocks via Indwelling Catheters to Predict Benefit from Thoracoscopic Splanchnicectomy in a Patient with Intractable Pancreatic Pain, Anesthesiology, Jun. 1995, 980-983, vol. 84.

Sweeney, James D., et al., An Asymmetric Two Electrode Cuff for Generation of Unidirectionally Propagated Action Potentials, IEEE Transactions on Biomedical Engineering, 1986, 541-549, vol. BME-33, No. 6.

Tataranni, P., From Physiology to Neuroendocrinology: A Reappraisal of Risk Factors of Body Weight Gain in Humans, Diabetes & Metabolism, Oct. 1997, 108-115, vol. 24, No. 2.

Terry, et al., An Implantable Neurocybernetic Prosthesis System, Epilepsia, 1990, pp. S33-S37, vol. 31, Suppl. 2.

Thoren, Peter, et al., Anodal block of medullated cardiopulmonary vagal afferents in cats, *J. Appl. Physiol.: Respir. Environ. Exercise Physiol.*, 1977, 461-465, vol. 42.

Tran, M.A., et al., Adrenergic Neurohumoral Influences of FFA Release From Bone Marrow Adipose Tissue, J. Pharmacol (Paris), 1985, 16, 2, 171-179.

University of Florida Research and Graduate Programs (RGP) website http://rgp.ufl.edu/otll/viewTech.html, Method and Apparatus for Allowing Selective Activity in Small Diameter Nerve Fibers.

Upton, et al., Autonomic Stimulation, PACE, Jan. 1991, 50-69, vol. 14.

Van Den Honert, et al., A Technique for Collision Block of Peripheral Nerve: Single Stimulus Analysis, IEEE Transactions on Biomedical Engineering, May 1981, 373-378, vol. BME-28, No. 5.

Van Den Honert, et al., Generation of Unidirectionally Propagated Action Potentials in a Peripheral Nerve by Brief Stimuli, Science, vol. 206, Dec. 14, 1979, pp. 1311-1312.

Wilkinson, H., Percutaneous Radiofrequency Upper Thorac Sympathectomy, Neurosurgey, Aug. 1994, 715-725, vol. 38, No. 4.

World J. Gastroenterol, Modulation of hypothalamic arcuate nucleus on gastric motility in rats, http://wjgnet.com, 4(5): 426-429, 1988.

Accornero, et al., Selective Activation of Peripheral Nerve Fibre Groups of Different Diameter by Triangular Shaped Stimulus Pulses, J. Physiol. (1977), 273, pp. 539-560, Great Britain.

Bolte, et al., Steroid Production from Plasma Cholesterol, II. In Vivo Conversion of Plasma Cholesterol to Ovarian Progesterone and Adrenal $C_{10}$ and $C_{21}$ Steroids in Humans; J Clin Endocrinal Metab (1974), pp. 394-400, vol. 38, No. 3 Montreal, Quebec, Canada.

Brillon, et al., Effect of Cortisol on Energy Expenditure and Amino Acid Metabolism in Humans; American Physiological Society, May 1994, pp. E501-E513, vol. 268.

Chen, et al., Induction of Leptin Resistance Through Direct Interaction of C-Reactive Protein with Leptin; Nature Medicin, vol. 12, No. 4, Apr. 2006, pp. 425-432.

Sato, et al, Novel Therapeutic Strategy Against Central Baroreflex Failure: A Bionic Baroreflex System; National Library of Medicine, Jul. 20, 1999; 100(3):299-304.

Woodbury, et al., Effects of Vagal Stimulation on Experimentally Induced Seizures in Rats; Epilepsia, 1990, pp. S7-S19, vol. 31, Suppl. 2, Raven Press, Ltd., New York.

Andrews, P. L., et al., "Interactions Between Splanchnic and Vagus Nerves in Control of Mean Intragastric Pressure in the Ferret", J. Physiol., vol. 351,(1984), pp. 473-490.

Becker, James M., "Myoelectric Control of Gastrointestinal and Biliary Motility: A Review", Surgery, vol. 89, No. 4,(1981), pp. 466-477.

Binks, A. P., et al., "High Strength Stimulation of the Vagus Nerve in Awake Humans: A Lack of Cardiorespiratory Effects", Respiration Physiology, vol. 127,(2001), pp. 125-133.

Non-Final Office Action for U.S. Appl. No. 10/920,734, Mailed on Aug. 7, 2009, pp. 12.

Non-Final Office Action for U.S. Appl. No. 10/920,734, Mailed on Jun. 30, 2008, pp. 6.

Non-Final Office Action for U.S. Appl. No. 10/785,726, Mailed on Jul. 25, 2007, pp. 9.

Final Office Action for U.S. Appl. No. 10/785,726, Mailed on Feb. 4, 2008, pp. 5.

Final Office Action for U.S. Appl. No. 10/785,726, Mailed on May 22, 2008, pp. 8.

Final Office Action for U.S. Appl. No. 10/785,726, Mailed on Dec. 24, 2008, pp. 11.

Notice of Allowance for U.S. Appl. No. 10/785,726, Mailed on May 14, 2009, pp. 8.

International Search Report for PCT Patent Application No. PCT/US2004/05057, Mailed on Feb. 15, 2006, pp. 2.

Office Action for Australian Patent Application No. 2004216247, Mailed on Sep. 25, 2008, 2 pages.

Office Action for Japanese Patent Application No. 2006-503742, Mailed on Aug. 12, 2009, 2 pages of Office Action and English translation of 2 pages.

International Search Report for PCT Patent Application No. PCT/US2001/00983, Mailed on May 9, 2001, pp. 3.

International Search Report for PCT Patent Application No. PCT/US2001/03319, Mailed on Jun. 12, 2001, p. 1.

International Search Report for PCT Patent Application No. PCT/US2000/40301, Mailed on Jan. 10, 2001, pp. 2.

International Search Report for PCT Patent Application No. PCT/US2001/29914, Mailed on Feb. 27, 2002, p. 1.

International Search Report for PCT Patent Application No. PCT/US2001/29892, Mailed on Mar. 13, 2002, p. 1.

International Search Report for PCT Patent Application No. PCT/US2005/29126, Mailed on Feb. 2, 2006, pp. 1.

Non-Final Office Action for U.S. Patent Application 11/338,388, Mailed on Apr. 16, 2009. pp. 9.

Final Office Action for U.S. Appl. No. 10/920,734, Mailed on Apr. 1, 2009, pp. 8.

International Preliminary Report on Patentability for PCT Patent Application No. PCT/US2007/01847, mailed on Aug. 7, 2008, pp. 12.

International Search Report for PCT Patent Application No. PCT/US2007/01847, Mailed on Nov. 19, 2007, pp. 3.

Non-Final Office Action for U.S. Appl. No. 11/657,877, Mailed on Jun. 19, 2009, pp. 14.

International Search Report for PCT patent Application No. PCT/US2007/13780, Mailed on Sep. 23, 2008, 1 page.

Adrian, T.E., et al., "Distributionand postprandial release of porcine peptide YY," J. Endocr., 1987, 113:11-14, Journal of Endocrinology Ltd., Great Britain.

Adrian, T.E., et al., "Human Distributionand Release f a Putative New Gut Hormone, Peptide YY," Gastroenterology, Nov. 1985, 89:1070-7, American Gastroenterlogical Association.

Castiglione, K.E., et al., "Food Intake Responses to Upper Gastrointestinal Lipid Infusions in Humans," Physiology & Behavior, 1998, 64(2): 141-5.

Cottrell, D.F., et el., "Tension receptors with vagal afferent fibres in the proximal duodenum and pyloric sphincter of sheep," J Physiol., 1984, 354:457-75 Great Britain.

Eissele, R. et al., "Glucagon-like peptide-1 cells in the gastrointestinal tract and pancreas of rat, pig, and man," European Journal of Clinical Investigation, 1992, 22:283-91.

Feinle, C., et al., "Effects of duodenal fat, protein or mixed-nutriet infusions on epigastric sensations during sustained gastric distension in healthy humans," Neurogastroenterol Mot., 2002, 14:205-13, Blackwell Science Ltd.

Feinle, C., et al., "Modulation of gastric distension-induced sensations by small intestinal receptors," Am J Physiol Gastrointest Liver Physiol, 2001, 280:G51-7.

Feinle, C., et al., "Relationship between increasing duodenal lipid doses, gastric perception, and plasma hormone levels in humans," Am J Physiol egulatory Intergratve Comp Physiol, 2000, 278:R1217-23, The American Physiological Soceity.

Feinle, C., et al., "Role of duodenal lipid and cholecystokinin A receptors in the pathophysiology of functional dyspspsia," Gut, 2001, 48:347-55.

Fink, A.S., et al., "Release of Human Pancreatic Polypeptide and Gastrin in Response to Intrduodenal Stimuli: A Case Report," Metabolism, Apr. 1979, 29(4): 339-42.

Fox, E.S., et al., "Neurotrophin-4 Deficient Mice Have a Loss of Vagal Intraganglionic Mechanoreceptors from the Small Intestine and a Disruption of Short-Term Satiety," Journal of Neuroscience, Nov. 1, 2001, 21(21):8602-15.

Hak, et al., "Associations of C-Reactive Protein With Measures of Obesity, Insulin resistance and Subclinical Atherosclerosis in Healthy, Middle-Aged Women," American heart Association, Arteriosclerosis, Thombosis and Bascular Biology, 1999; 19; 1986-1991.

Kral, et al., "Gastrophlasty for Obesity:Long-Term Weight Loss Improved by Vagotomy," World Journal of Surgery, vol. 17, No. 1, Jan./Feb. 1993, pp. 17 and 75-79.

Lemieux, et al., "Elevated C-Reactive Protein: Another Component of the Artherothrombotic Profile of Abdominal Obseity," American Heart Association, Arteriosclerosis, Thrombosis and Vascular Biology, 2001; 21; 961-967.

Lingenfelser, T., et al., "Effects of duodenal distension on antropyloroduodenal pressures and perception are modified by hyperglycemia," Am J Physiol, 1999, 276, G711-G718.

Lloyd, K.C., et al., "Duodenal lipid inhibits gastric acid secretion by vagal, capsaicin-sensitive afferent pathways in rats," Am J Physiol., 1993, 27:G659-63.

MacDonald, K.G., et al., "The Gastric Bypass Operation educes the Progression and Mortality of Non-Insulin-Dependent Diabetes Mellitus," J Gastrointest Surg, May 1, 1997, 1(3):213-220.

Maddison, S., et al., "Hypothalamic Unit Responses to Alimentary Perfusions in the Anesthetised Rat," Brain Research Bulletin, 1979, 4(2): 259-66.

Pilichiewicz, A., et al., Effect of lipase inhibition on gastric emptying of, and the glycemic and incretin responses to, an oil/aquenos drink in type 2 diabetes mellitus, J Clin Endocrinol Metab, 2003, 88:3829-34.

Reidelberger, R.D., et al., "Postgastric satiety in the sham-feeding rat," Am J Physiol Regulatory Intergrative Comp Physiol, 1983, 244:872-81.

Rosengurt, S.V., "Expression of bitter taste receptors of the T2R family in the gastrointestinal tract and enteroendocrine STC-1 cells," Proc Natl Acad Sci U S A, 2002, 99, 2392-97.

Shafik, A., "Effect of Duodenal Distension on the Pyloric Sphincter and Antrum and the Gastric Corpus: Duodenopyloric Relfex," World J Surg, 1998, 22:1061-4.

Visser, et al., "Elevated C-Reactive Protein levels in Overweight and Obese Adults," JAMA, 1999; 282(2): 2131-2135.

U.S. Appl. No. 60/729,770, entitled Biliary/Pancreatic Shunt Device and Method for Treatment of Metabolic and other Diseases filed Oct. 24, 2005.

Final Office Action for U.S. Appl. No. 11/422,019, Mailed on Jun. 29, 2009, pp. 13.

Non-Final Office Action for U.S. Appl. No. 11/422,019, Mailed on Nov. 19, 2008, pp. 8.

International Preliminary Report on Patentability for PCT Patent Application No. PCT/US2007/01847, mailed on Aug. 7, 2008, pp. 12.

* cited by examiner

PULSE GENERATOR SCHEMATIC

*FIG. 5*

CATHETER-TYPE LEAD/ELECTRODE ASSEMBLY

ELECTRIC MODULATION OF SYMPATHETIC NERVOUS SYSTEM

CROSS REFERENCE TO RELATED APPLICATIONS

This application is a divisional, and claims the benefit of priority under 35 U.S.C. sctn. 120, of U.S. patent application Ser. No. 10/243,612, filed on Sep. 13, 2002, now U.S. Pat. No. 7,239,912, and titled "ELECTRIC MODULATION OF SYMPATHETIC NERVOUS SYSTEM," which claims the benefit of U.S. Provisional Patent Application Ser. No. 60/366,750, filed on Mar. 22, 2002, and entitled "Sympathetic Nervous System Electrical Stimulation for Weight Control"; U.S. Provisional Patent Application Ser. No. 60/370,311, filed on Apr. 5, 2002, and entitled "Splanchnic Nerve Stimulation and Anchoring to the Crus of the Diaphragm for Obesity Treatment"; U.S. Provisional Patent Application Ser. No. 60/379,605, filed on May 10, 2002, and entitled "Percutaneous Placement of an Electrode for Splanchnic Nerve Stimulation with and without Thorascopic Visualization for Obesity and Diabetes Therapy"; U.S. Provisional Patent Application Ser. No. 60/384,219, filed on May 30, 2002, and entitled "Sympathetic Nervous System Electrical Stimulation for Weight Control"; and U.S. Provisional Patent Application Ser. No. 60/386,699, filed on Jun. 10, 2002, and entitled "Treatment of Obesity and Other Medical Conditions Through Electrical Nerve Modulation of the Sympathetic Nervous System," the entireties of all of which are hereby incorporated by reference.

BACKGROUND OF THE INVENTION

1. Field of the Invention

This invention is in the field of nerve stimulation for the treatment of medical conditions.

2. Background Art

Obesity is considered an epidemic in the U.S. with a prevalence of 19.8%. The annual healthcare costs associated with obesity are estimated to exceed $200 BB. Obesity is defined as a body mass index (BMI) that exceeds 30 kg/m2. Normal BMI is 18.5-25 kg/m2 and overweight persons have BMIs of 25-30. Obesity is classified into three groups moderate (Class 1), severe (Class II), and very severe (Class III). Patients with BMIs that exceed 30 are at risk for significant comorbidities such as diabetes, heart and kidney disease, dyslipidemia, hypertension, sleep apnea, and orthopedic problems.

Obesity results from an imbalance between food intake and energy expenditure such that there is a net increase in fat reserves. Excessive food intake, reduced energy expenditure, or both may cause this imbalance. Appetite and satiety, which control food intake, are partly controlled in the brain by the hypothalamus. Energy expenditure is also partly controlled by the hypothalamus. The hypothalamus regulates the autonomic nervous system of which there are two branches, the sympathetic and the parasympathetic. The sympathetic nervous system generally prepares the body for action by increasing heart rate, blood pressure, and metabolism. The parasympathetic system prepares the body for rest by lowering heart rate, lowering blood pressure, and stimulating digestion. Destruction of the lateral hypothalamus results in hunger suppression, reduced food intake, weight loss, and increased sympathetic activity. In contrast, destruction of the ventromedial nucleus of the hypothalamus results in suppression of satiety, excessive food intake, weight gain, and decreased sympathetic activity. The splanchnic nerves carry sympathetic neurons that supply, or innervate, the organs of digestion and adrenal glands, and the vagus nerve carries parasympathetic neurons that innervate the digestive system and are involved in the feeding and weight gain response to hypothalamic destruction.

Experimental and observational evidence suggests that there is a reciprocal relationship between food intake and sympathetic nervous system activity. Increased sympathetic activity reduces food intake and reduced sympathetic activity increases food intake. Certain peptides (e.g. neuropeptide Y, galanin) are known to increase food intake while decreasing sympathetic activity. Others such as cholecystokinin, leptin, enterostatin, reduce food intake and increase sympathetic activity. In addition, drugs such as nicotine, ephedrine, caffeine, subitramine, dexfenfluramine, increase sympathetic activity and reduce food intake.

Ghrelin is another peptide that is secreted by the stomach that is associated with hunger. Peak plasma levels occur just prior to meal time, and ghrelin levels are increased after weight loss. Sympathetic activity may suppress ghrelin secretion.

Appetite is stimulated by various psychosocial factors, but is also stimulated by low blood glucose levels. Cells in the hypothalamus that are sensitive to glucose levels are thought to play a role in hunger stimulation. Sympathetic activity increases plasma glucose levels. Satiety is promoted by distension of the stomach and delayed gastric emptying. Sympathetic activity reduces duodenal motility and increases pyloric sphincter, which may result in distention and delayed gastric emptying.

The sympathetic nervous system plays a role in energy expenditure and obesity. Genetically inherited obesity in rodents is characterized by decreased sympathetic activity to adipose tissue and other peripheral organs. Catecholamines and cortisol, which are released by the sympathetic nervous system, cause a dose-dependent increase in resting energy expenditure. In humans, there is a reported negative correlation between body fat and plasma catecholamine levels. Overfeeding or underfeeding lean human subjects has a significant effect on energy expenditure and sympathetic nervous system activation. For example, weight loss in obese subjects is associated with a compensatory decrease in energy expenditure, which promotes the regain of previously lost weight. Drugs that activate the sympathetic nervous system, such as ephedrine, caffeine and nicotine, are known to increase energy expenditure. Smokers are known to have lower body fat stores and increased energy expenditure.

The sympathetic nervous system also plays an important role in regulating energy substrates for increased expenditure, such as fat and carbohydrate. Glycogen and fat metabolism are increased by sympathetic activation and are needed to support increased energy expenditure.

Animal research involving acute electrical activation of the splanchnic nerves under general anesthesia causes a variety of physiologic changes. Electrical activation of a single splanchnic nerve in dogs and cows causes a frequency dependent increase in catecholamine, dopamine, and cortisol secretion. Plasma levels can be achieved that cause increased energy expenditure. In adrenalectomized anesthetized pigs, cows, and dogs, acute single splanchnic nerve activation causes increased blood glucose and reduction in glycogen liver stores. In dogs, single splanchnic nerve electrical activation causes increased pyloric sphincter tone and decrease duodenal motility. Sympathetic and splanchnic nerve activation can cause suppression of insulin and leptin hormone secretion.

First line therapy for obesity is behavior modification involving reduced food intake and increased exercise. However, these measures often fail and behavioral treatment is supplemented with pharmacologic treatment using the pharmacologic agents noted above to reduce appetite and increase energy expenditure. Other pharmacologic agents that may cause these affects include dopamine and dopamine analogs, acetylcholine and cholinesterase inhibitors. Pharmacologic therapy is typically delivered orally and results in systemic side effects such as tachycardia, sweating, and hypertension. In addition, tolerance can develop such that the response to the drug reduces even at higher doses.

More radical forms of therapy involve surgery. In general, these procedures reduce the size of the stomach and/or reroute the intestinal system to avoid the stomach. Representative procedures are gastric bypass surgery and gastric banding. These procedures can be very effective in treating obesity, but they are highly invasive, require significant lifestyle changes, and can have severe complications.

Experimental forms of treatment for obesity involve electrical stimulation of the stomach (gastric pacing) and the vagus nerve (parasympathetic system). These therapies use a pulse generator to electrically stimulate the stomach or vagus nerve via implanted electrodes. The intent of these therapies is to reduce food intake through the promotion of satiety and or reduction of appetite, and neither of these therapies is believed to affect energy expenditure. U.S. Pat. No. 5,423,872 to Cigaina describes a method for treating eating disorders by electrically pacing the stomach. The believed mechanism of action is the promotion of satiety by reducing gastric activity and consequently delaying stomach content emptying. Reduction of appetite may also occur, but this is unclear. U.S. Pat. No. 5,263,480 to Wernicke discloses a method for treating obesity by electrically activating the vagus nerve. This therapy may promote satiety as afferent fibers that are stimulated by stomach distention are carried in the vagus nerve. Neither of these therapies increases energy expenditure.

BRIEF SUMMARY OF THE INVENTION

The present invention includes a method for treating obesity or other disorders by electrically activating the sympathetic nervous system. Obesity can be treated by activating the efferent sympathetic nervous system, thereby increasing energy expenditure and reducing food intake. Stimulation is accomplished using a pulse generator and electrodes implanted near, or attached to, various areas of the sympathetic nervous system, such as the sympathetic chain ganglia, the splanchnic nerves (greater, lesser, least), or the peripheral ganglia (eg. celiac, mesenteric). Ideally, the obesity therapy will employ electrical activation of the sympathetic nervous system that innervates the digestive system, adrenals, and abdominal adipose tissue, such as the splanchnic nerves or celiac ganglia.

This method of obesity treatment may reduce food intake by a variety of mechanisms, including general increased sympathetic system activation and increasing plasma glucose levels upon activation. Satiety may be produced through direct affects on the pylorus and duodenum that cause stomach distension and delayed stomach emptying. In addition, food intake may be reduced by reducing ghrelin secretion.

This method of obesity treatment may also increase energy expenditure by causing catecholamine, cortisol, and dopamine release from the adrenal glands. The therapy could be titrated to the release of these hormones. Fat and carbohydrate metabolism, which are also increased by sympathetic nerve activation, will accompany the increased energy expenditure.

Other hormonal effects induced by this therapy may include reduced insulin secretion. Alternatively, this method may be used to normalize catecholamine levels, which are reduced with weight gain.

Electrical sympathetic activation for treating obesity is ideally accomplished without causing a rise in mean arterial blood pressure (MAP). This may be achieved by using an appropriate stimulation pattern with a relatively short signal-on time followed by an equal or longer signal-off time. During activation therapy, a sinusoidal-like fluctuation in the MAP may occur with an average MAP that is within safe limits. Alternatively, an alpha sympathetic receptor blocker, such as prazosin, could be used to blunt the increase in MAP.

Electrical sympathetic activation may be titrated to the plasma level of catecholamines achieved during therapy. This would allow the therapy to be monitored and safe levels of increased energy expenditure to be achieved. The therapy could also be titrated to plasma ghrelin levels.

Electrical modulation (inhibition or activation) of the sympathetic nerves can also be used to treat other eating disorders such as anorexia or bulimia. For example, inhibition of the sympathetic nerves may be useful in treating anorexia. Electrical modulation of the sympathetic nerves may also be used to treat gastrointestinal diseases such as peptic ulcers, esophageal reflux, gastroparesis, and irritable bowel. For example, stimulation of the splanchnic nerves that innervate the large intestine may reduce the symptoms of irritable bowel syndrome, characterized by diarrhea. Pain may also be treated by electric nerve modulation of the sympathetic nervous system, as certain pain neurons are carried in the sympathetic nerves. This therapy may also be used to treat type II diabetes. These conditions may require varying degrees of inhibition or stimulation.

The novel features of this invention, as well as the invention itself, will be best understood from the attached drawings, taken along with the following description, in which similar reference characters refer to similar parts, and in which:

DETAILED DESCRIPTION OF THE INVENTION

The human nervous system is a complex network of nerve cells, or neurons, found centrally in the brain and spinal cord and peripherally in the various nerves of the body. Neurons have a cell body, dendrites and an axon. A nerve is a group of neurons that serve a particular part of the body. Nerves may contain several hundred neurons to several hundred thousand neurons. Nerves often contain both afferent and efferent neurons. Afferent neurons carry signals back to the central nervous system and efferent neurons carry signals to the periphery. A group of neuronal cell bodies in one location is known as a ganglion. Electrical signals are conducted via neurons and nerves. Neurons release neurotransmitters at synapses (connections) with other nerves to allow continuation and modulation of the electrical signal. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it.

Neurons can be myelinated and unmyelinated, of large axonal diameter and small axonal diameter. In general, the speed of action potential conduction increases with myelination and with neuron axonal diameter. Accordingly, neurons are classified into type A, B and C neurons based on myelination, axon diameter, and axon conduction velocity. In terms of axon diameter and conduction velocity, A is greater than B which is greater than C.

Figure 1:
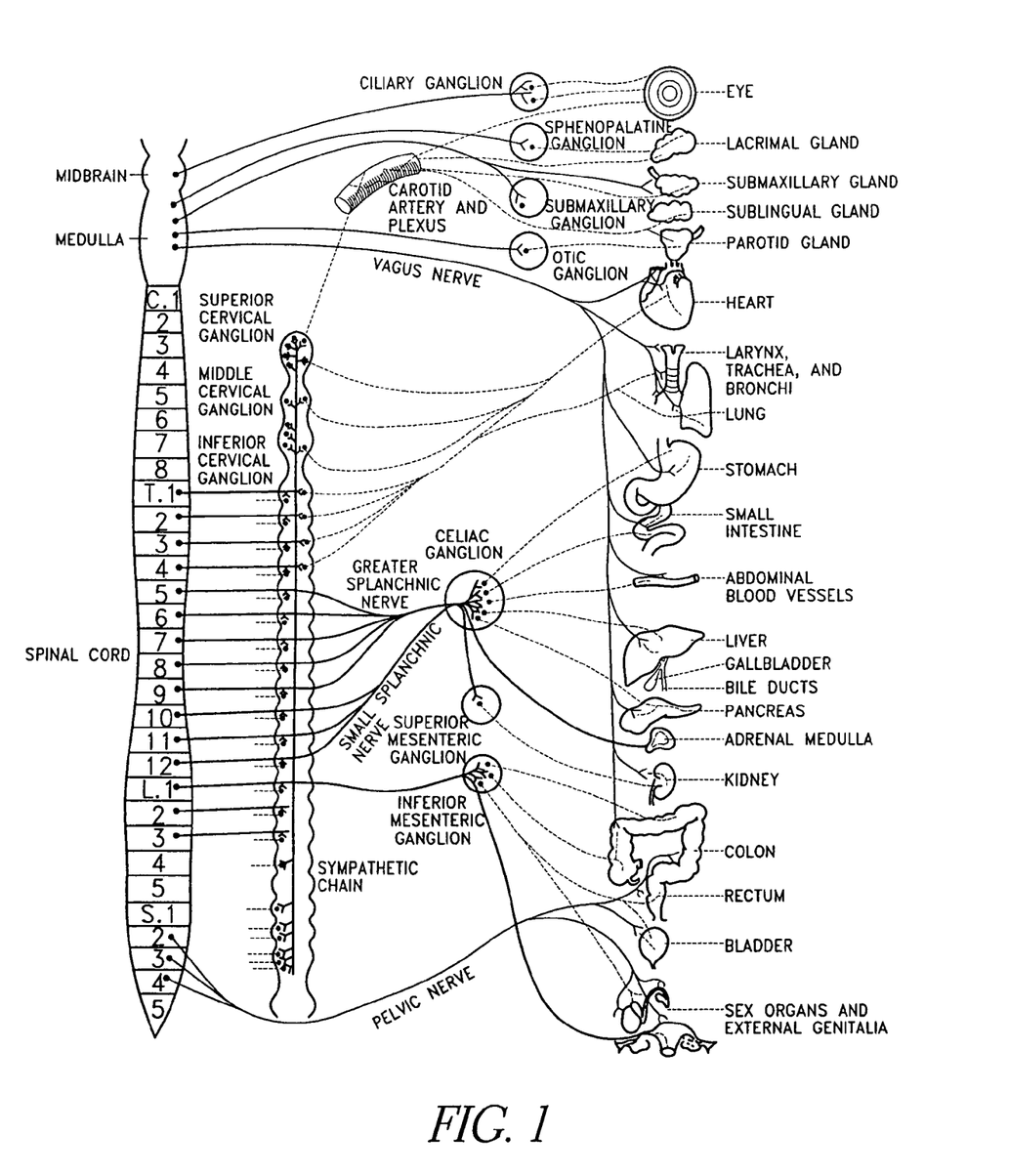
FIG. 1 is a diagram of the efferent autonomic nervous system.

The autonomic nervous system is a subsystem of the human nervous system that controls involuntary actions of the smooth muscles (blood vessels and digestive system), the heart, and glands, as shown in FIG. 1. The autonomic nervous system is divided into the sympathetic and parasympathetic systems. The sympathetic nervous system generally prepares the body for action by increasing heart rate, increasing blood pressure, and increasing metabolism. The parasympathetic system prepares the body for rest by lowering heart rate, lowering blood pressure, and stimulating digestion.

Figure 2:
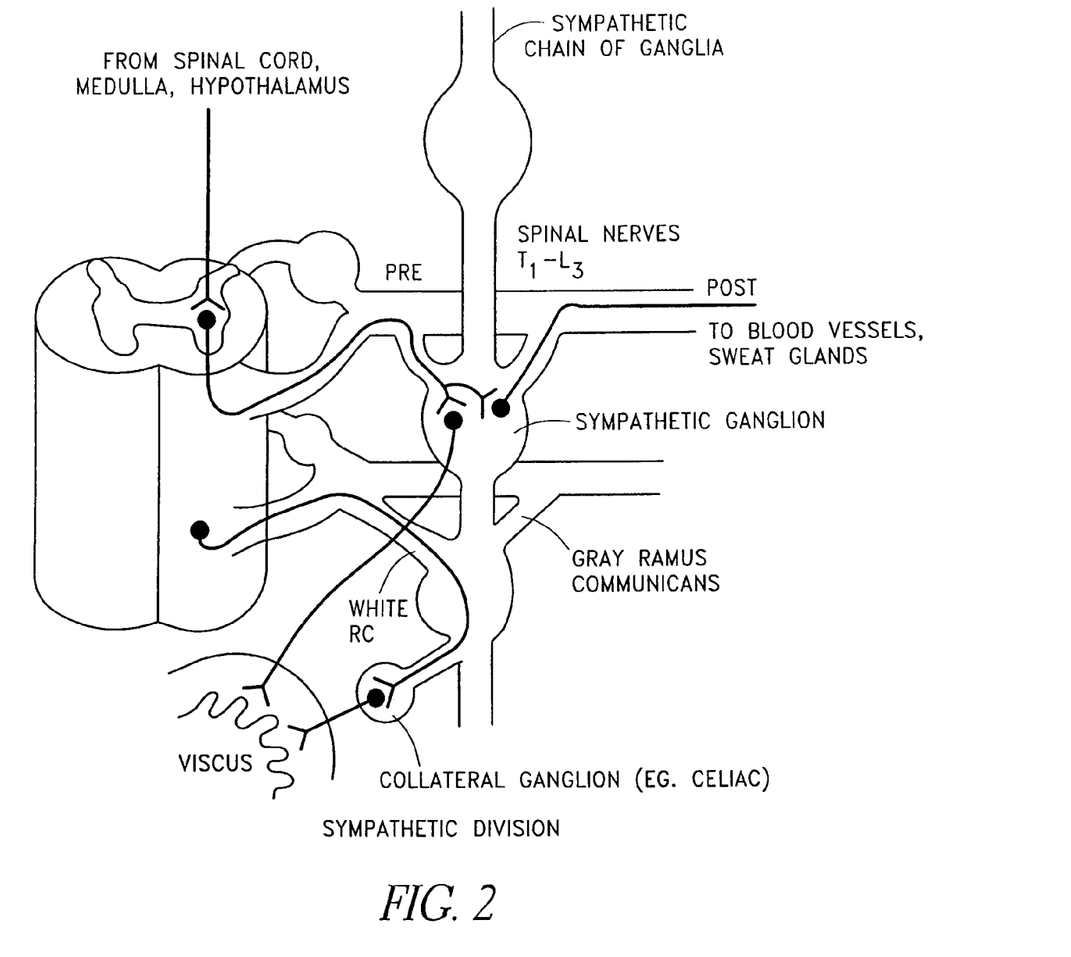
FIG. 2 is a diagram of sympathetic nervous system anatomy.

The hypothalamus controls the sympathetic nervous system via descending neurons in the ventral horn of the spinal cord, as shown in FIG. 2. These neurons synapse with preganglionic sympathetic neurons that exit the spinal cord and form the white communicating ramus. The preganglionic neuron will either synapse in the paraspinous ganglia chain or pass through these ganglia and synapse in a peripheral, or collateral, ganglion such as the celiac or mesenteric. After synapsing in a particular ganglion, a postsynaptic neuron continues on to innervate the organs of the body (heart, intestines, liver, pancreas, etc.) or to innervate the adipose tissue and glands of the periphery and skin. Preganglionic neurons of the sympathetic system are typically myelinated type B neurons and postganglionic neurons are typically unmyelinated type C neurons.

Figure 3:
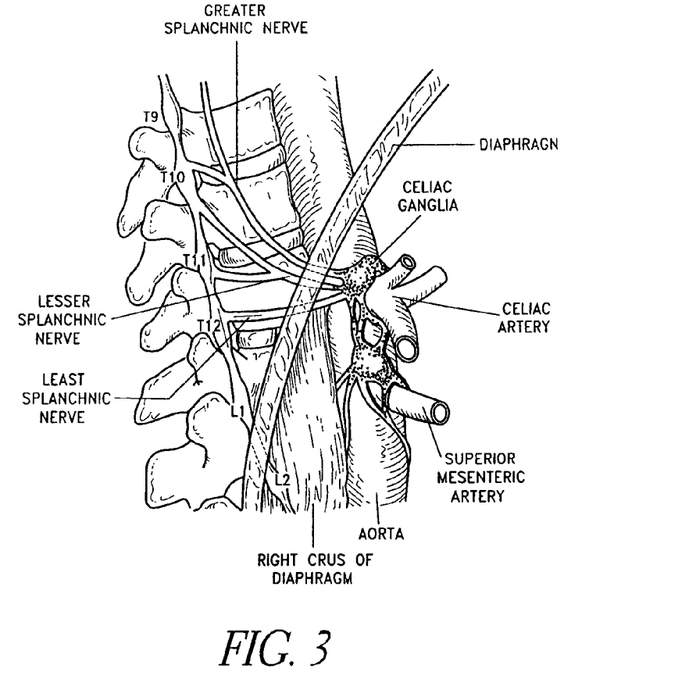
FIG. 3 is an elevation view of the splanchnic nerves and celiac ganglia.

Several large sympathetic nerves and ganglia are formed by the neurons of the sympathetic nervous system as shown in FIG. 3. The greater splanchnic nerve (GSN) is formed by efferent sympathetic neurons exiting the spinal cord from thoracic vertebral segment numbers 4 or 5 (T4 or T5) through thoracic vertebral segment numbers 9 or 10 or 11 (T9, T10, or T11). The lesser splanchnic (lesser SN) nerve is formed by preganglionic fibers sympathetic efferent fibers from T10 to T12 and the least splanchnic nerve (least SN) is formed by fibers from T12. The GSN is typically present bilaterally in animals, including humans, with the other splanchnic nerves having a more variable pattern, present unilaterally or bilaterally and sometimes being absent. The splanchnic nerves run along the anterior-lateral aspect of the vertebral bodies and pass out of the thorax and enter the abdomen through the crus of the diaphragm. The nerves run in proximity to the azygous veins. Once in the abdomen, neurons of the GSN synapse with postganglionic neurons primarily in celiac ganglia. Some neurons of the GSN pass through the celiac ganglia and synapse on in the adrenal medulla. Neurons of the lesser SN and least SN synapse with post-ganglionic neurons in the mesenteric ganglia.

Postganglionic neurons, arising from the celiac ganglia that synapse with the GSN, innervate primarily the upper digestive system, including the stomach, pylorus, duodenum, pancreas, and liver. In addition, blood vessels and adipose tissue of the abdomen are innervated by neurons arising from the celiac ganglia/greater splanchnic nerve. Postganglionic neurons of the mesenteric ganglia, supplied by preganglionic neurons of the lesser and least splanchnic nerve, innervate primarily the lower intestine, colon, rectum, kidneys, bladder, and sexual organs, and the blood vessels that supply these organs and tissues.

In the treatment of obesity, the preferred embodiment involves electrical activation of the greater splanchnic nerve of the sympathetic nervous system. Preferably unilateral activation would be utilized, although bilateral activation could also be utilized. The celiac ganglia could also be activated, as well as the sympathetic chain or ventral spinal roots.

Electrical nerve modulation (nerve activation or inhibition) is accomplished by applying an energy signal (pulse) at a certain frequency to the neurons of a nerve (nerve stimulation). The energy pulse causes depolarization of neurons within the nerve above the activation threshold resulting in an action potential. The energy applied is a function of the current amplitude and pulse width duration. Activation or inhibition can be a function of the frequency, with low frequencies on the order of 1 to 50 Hz resulting in activation and high frequencies greater than 100 Hz resulting in inhibition. Inhibition can also be accomplished by continuous energy delivery resulting in sustained depolarization. Different neuronal types may respond to different frequencies and energies with activation or inhibition.

Each neuronal type (i.e., type A, B, or C neurons) has a characteristic pulse amplitude-duration profile (energy pulse signal) that leads to activation. Myelinated neurons (types A and B) can be stimulated with relatively low current amplitudes on the order of 0.1 to 5.0 milliamperes and short pulse widths on the order of 50 to 200 microseconds. Unmyelinated type C fibers typically require longer pulse widths on the order of 300 to 1,000 microseconds and higher current amplitudes. This difference in energy for activation can be utilized to selectively stimulate certain neurons in a nerve containing mixed neuronal types. This can be important in stimulating nerves such as the splanchnic, because the splanchnic nerves contains both afferent pain neurons, which are typically type C neurons, and efferent pre-ganglionic neurons, which are myelinated type B. If a therapy such as obesity treatment involves splanchnic nerve activation, it would be desirable to activate the efferent type B neurons and not the afferent type C pain neurons. This may be accomplished by varying the energy pulse signal.

Two important parameters related to stimulation of peripheral nerves of mixed neuronal type are the rheobase and chronaxie. These two parameters are a function of the stimulus duration and stimulus strength (current amplitude). The rheobase is the lower limit of the stimulus strength below which an action potential cannot be generated, regardless of the stimulus duration. The chronaxie is the stimulus duration corresponding to twice the rheobase. This is a measure of excitability of the mixed peripheral nerve. It is not desirable to stimulate a peripheral nerve at stimulus intensities greater than the chronaxie. The chronaxie of the splanchnic nerve is likely between approximately 150 microseconds and 400 microseconds.

Figure 4:
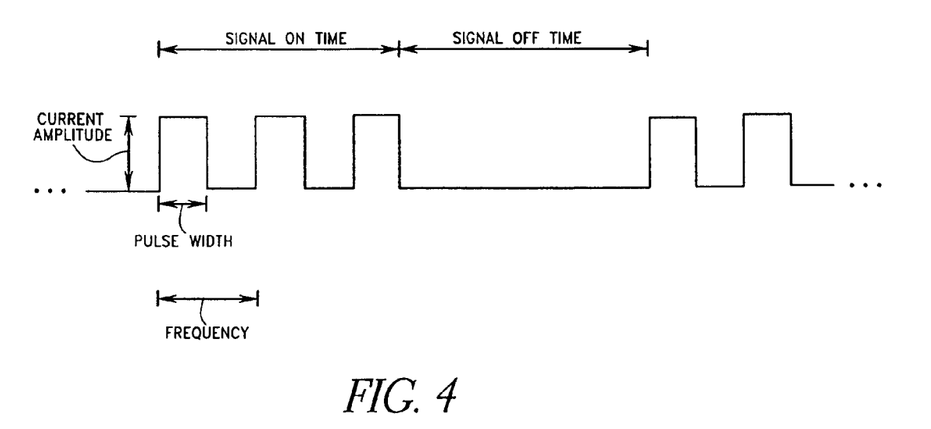
FIG. 4 is a schematic of an exemplary prior art stimulation pattern which can be used in the method of the present invention.

Various stimulation patterns, ranging from continuous to intermittent, can be utilized. With intermittent stimulation, energy is delivered for a period of time at a certain frequency during the signal-on time as shown in FIG. 4. The signal-on time is followed by a period of time with no energy delivery, referred to as signal-off time.

Superimposed on the stimulation pattern are the treatment parameters, frequency and duration. The treatment frequency may be continuous or delivered at various time periods within the day or week. The treatment duration may last for as little as a few minutes to as long as several hours. For example, splanchnic nerve activation to treat obesity may be delivered at a frequency of three times daily, coinciding with meal times. Treatment duration with a specified stimulation pattern may last for one hour. Alternatively, treatment may be delivered at a higher frequency, say every three hours, for shorter durations, say 30 minutes. The treatment duration and frequency can be tailored to achieve the desired result.

Pulse generation for electrical nerve modulation is accomplished using a pulse generator. Pulse generators can use conventional microprocessors and other standard electrical components. A pulse generator for this embodiment can generate a pulse, or energy signal, at frequencies ranging from approximately 0.5 Hz to 300 Hz, a pulse width from approximately 10 to 1,000 microseconds, and a constant current of between approximately 0.1 milliamperes to 20 milliamperes. The pulse generator may be capable of producing a ramped, or sloped, rise in the current amplitude. The preferred pulse generator can communicate with an external programmer and or monitor. Passwords, handshakes and parity checks are employed for data integrity. The pulse generator can be battery operated or operated by an external radiofrequency device. Because the pulse generator, associated components, and battery may be implanted they are preferably encased in an epoxy-titanium shell.

Figure 5:
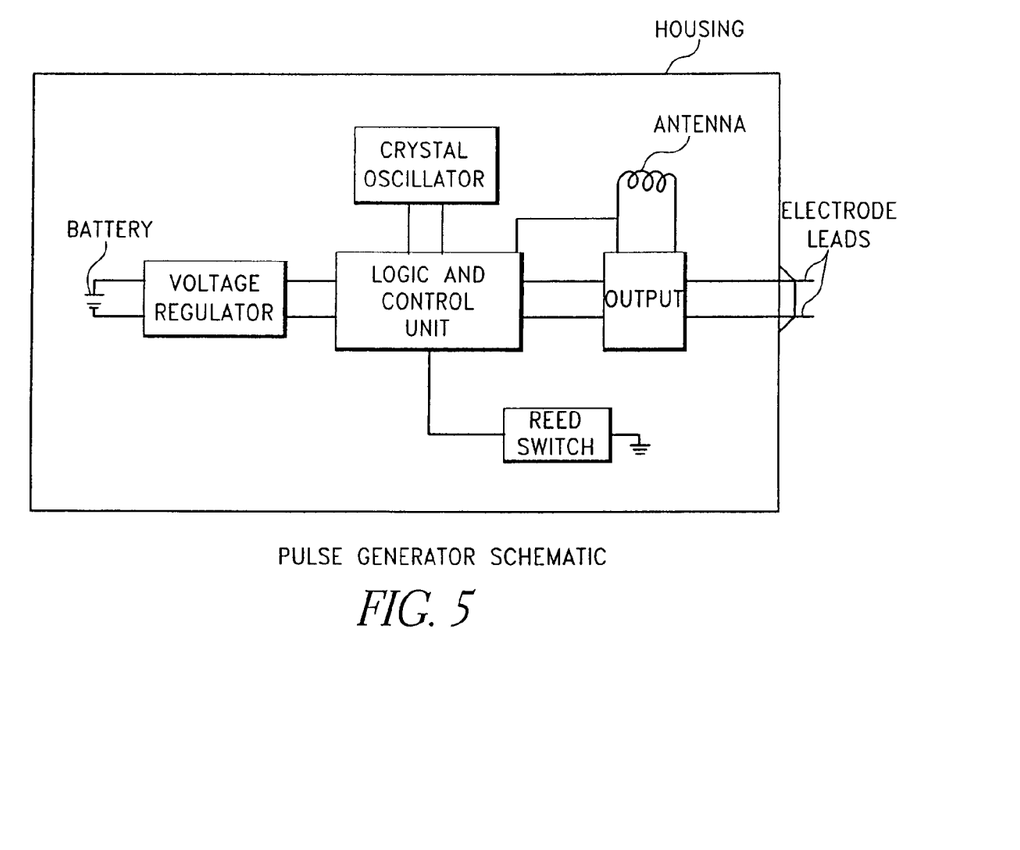
FIG. 5 is a schematic of an exemplary prior art pulse generator which can be used in the method of the present invention.

A schematic of the implantable pulse generator (IPG) is shown in FIG. 5. Components are housed in the epoxy-titanium shell. The battery supplies power to the logic and control unit. A voltage regulator controls the battery output. The logic and control unit control the stimulus output and allow for programming of the various parameters such as pulse width, amplitude, and frequency. In addition, the stimulation pattern and treatment parameters can be programmed at the logic and control unit. A crystal oscillator provides timing signals for the pulse and for the logic and control unit. An antenna is used for receiving communications from an external programmer and for status checking the device. The output section couples to the electrodes and leads that carry the energy pulse to the nerve. The reed switch allows manual activation using an external magnet. Devices powered by an external radiofrequency device would limit the components to primarily a receiving coil or antenna.

The IPG is coupled to a lead and electrode assembly. The lead is a bundle of electrically conducting wires insulated from the surroundings by a non-electrically conducting coating. The wires of the lead connect the IPG to the stimulation electrodes, which transfers the energy pulse to the nerve. A single wire may connect the IPG to the electrode, or a wire bundle may connect the IPG to the electrode. Wire bundles may or may not be braided. Wire bundles are preferred because they increase reliability and durability. Alternatively, a helical wire assembly could be utilized to improve durability with flexion and extension of the lead.

Figure 6:
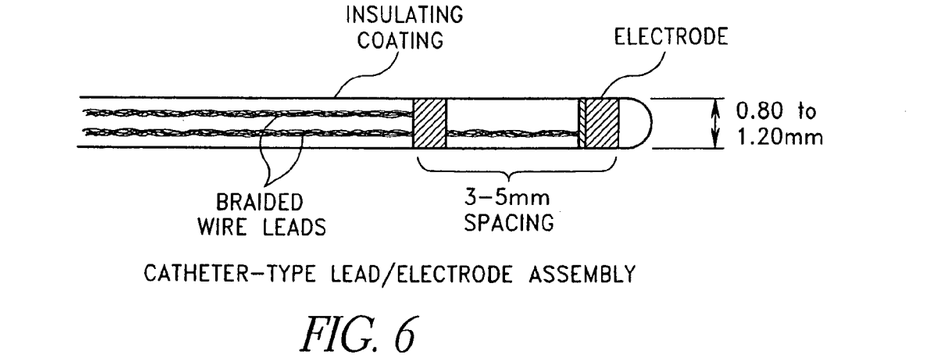
FIG. 6 is a sketch of an exemplary prior art catheter-type lead and electrode assembly which can be used in the method of the present invention.

The electrodes are preferably platinum or platinum-iridium ribbons or rings as shown in FIG. 6. The electrodes are capable of electrically coupling with the surrounding tissue and nerve. The electrodes may encircle a catheter-like lead assembly. The distal electrode may form a rounded cap at the end to create a bullet nose shape. Ideally, this electrode serves as the cathode. A lead of this type may contain 2 to 4 ring electrodes spaced anywhere from 2.0 to 5.0 mm apart with each ring electrode being approximately 1.0 to 10.0 mm in width. Catheter lead electrode assemblies may have an outer diameter of 0.5 mm to 1.5 mm to facilitate percutaneous placement using an introducer.

Bipolar stimulation of a nerve can be accomplished with multiple electrode assemblies with one electrode serving as the positive node and the other serving as a negative node. In this manner nerve activation can be directed primarily in one direction (unilateral), such as efferently, or away from the central nervous system. Alternatively, a nerve cuff electrode can be employed. Helical cuff electrodes as described in U.S. Pat. No. 5,251,634 to Weinberg are preferred. Cuff assemblies can similarly have multiple electrodes and direct and cause unilateral nerve activation.

Unipolar stimulation can also be performed. As used herein, unipolar stimulation means using only a single electrode on the lead, while the metallic shell of the IPG, or another external portion of the IPG, essentially functions as a second electrode, remote from the first electrode. This type of unipolar stimulation may be more suitable for splanchnic nerve stimulation than the bipolar stimulation method, particularly if the electrode is to be placed percutaneously under fluoroscopic visualization. With fluoroscopically observed percutaneous placement, it may not always be possible to place the electrodes immediately adjacent the nerve, which can be required for bipolar stimulation. With unipolar stimulation, a larger energy field is created in order to electrically couple the electrode on the lead with the remote external portion of the IPG, and the generation of this larger energy field can result in activation of the nerve even in the absence of close proximity between the single lead electrode and the nerve. This allows successful nerve stimulation with the single electrode placed only in "general proximity" to the nerve, meaning that there can be significantly greater separation between the electrode and the nerve than the "close proximity" required for bipolar stimulation. The magnitude of the allowable separation between the electrode and the nerve will necessarily depend upon the actual magnitude of the energy field which the operator generates with the lead electrode in order to couple with the remote electrode.

In multiple electrode lead assemblies, some of the electrodes may be used for sensing nerve activity. This sensed nerve activity could serve as a signal to commence stimulation therapy. For example, afferent action potentials in the splanchnic nerve, created due to the commencement of feeding, could be sensed and used to activate the IPG to begin stimulation of the efferent neurons of the splanchnic nerve. Appropriate circuitry and logic for receiving and filtering the sensed signal would be required in the IPG.

Because branches of the splanchnic nerve directly innervate the adrenal medulla, electrical activation of the splanchnic nerve results in the release of catecholamines (epinephrine and norepinephrine) into the blood stream. In addition, dopamine and cortisol, which also raise energy expenditure, can be released. Catecholamines can increase energy expenditure by 15% to 20%. By comparison, subitramine, a pharmacologic agent used to treat obesity, increases energy expenditure by only 3% to 5%.

Figure 7:
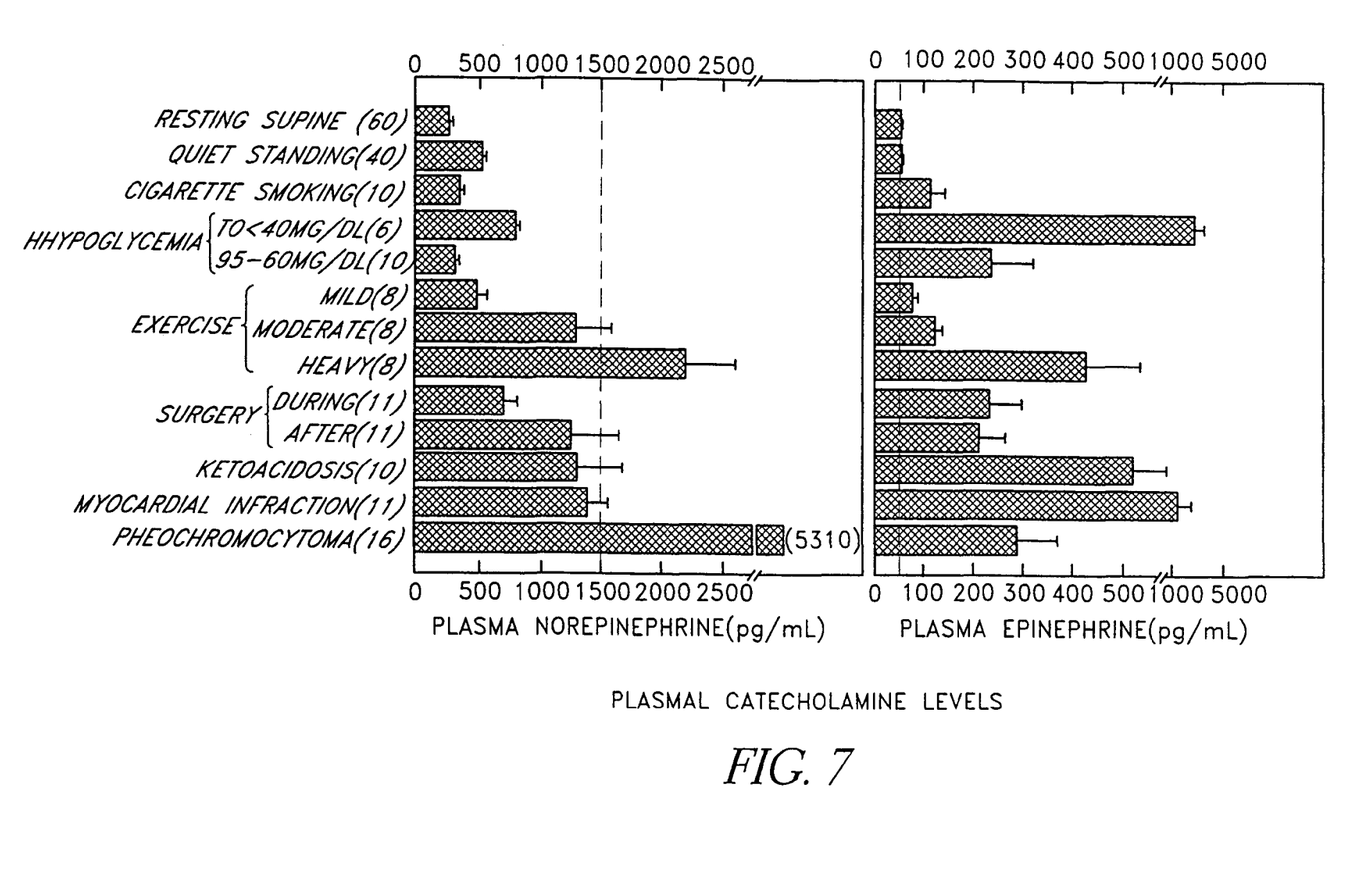
FIG. 7 is a graph of known plasmal catecholamine levels in various physiologic and pathologic states.

Human resting venous blood levels of norepinephrine and epinephrine are approximately 25 picograms (pg)/milliliter (ml) and 300 pg/ml, respectively, as shown in FIG. 7. Detectable physiologic changes such as increased heart rate occur at norepinephrine levels of approximately 1,500 pg/ml and epinephrine levels of approximately 50 pg/ml. Venous blood levels of norepinephrine can reach as high 2,000 pg/ml during heavy exercise, and levels of epinephrine can reach as high as 400 to 600 pg/ml during heavy exercise. Mild exercise produces norepinephrine and epinephrine levels of approximately 500 pg/ml and 100 pg/ml, respectively. It may be desirable to maintain catecholamine levels somewhere between mild and heavy exercise during electrical sympathetic activation treatment for obesity.

Figure 8A:
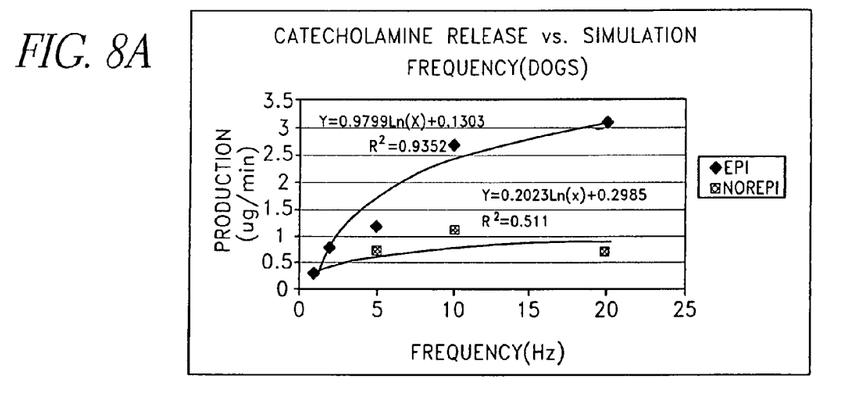
FIGS. 8A, 8B, and 8C are exemplary graphs of the effect of splanchnic nerve stimulation on catecholamine release rates, epinephrine levels, and energy expenditure, respectively, which can be achieved in the practice of the present invention.
Figure 8B:
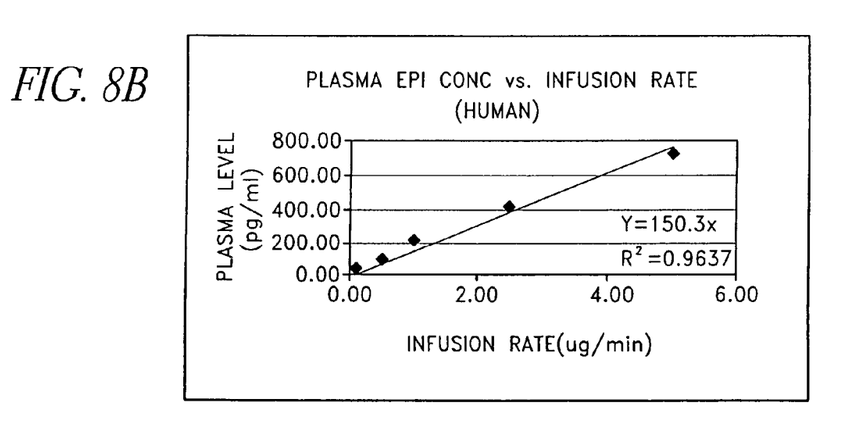
Figure 8C:
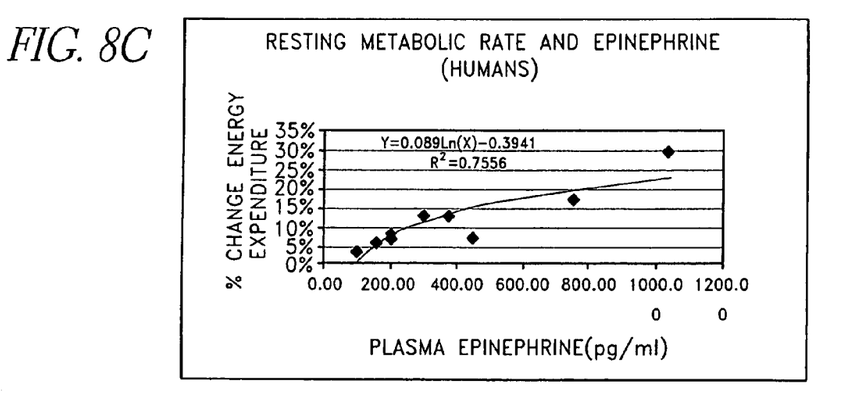

In anesthetized animals, electrical stimulation of the splanchnic nerve has shown to raise blood catecholamine levels in a frequency dependent manner in the range of 1 Hz to 20 Hz, such that rates of catecholamine release/production of 0.3 to 4.0 μg/min can be achieved. These rates are sufficient to raise plasma concentrations of epinephrine to as high as 400 to 600 pg/ml, which in turn can result in increased energy expenditure ranging from 10% to 20% as shown in FIG. 8. During stimulation, the ratio of epinephrine to norepinephrine is 65% to 35%. It may be possible to change the ratio by stimulating at higher frequencies. This may be desired to alter the energy expenditure and/or prevent a rise in MAP.

Energy expenditure in humans ranges from approximately 1.5 kcal/min to 2.5 kcal/min. A 15% increase in this energy expenditure in a person with a 2.0 kcal/min energy expenditure would increase expenditure by 0.3 kcal/min. Depending on treatment parameters, this could result in an additional 100 to 250 kcal of daily expenditure and 36,000 to 91,000 kcal of yearly expenditure. One pound of fat is approximately 3500 kcal, yielding an annual weight loss of 10 to 26 pounds.

Increased energy expenditure would need to be fueled by fat and carbohydrate metabolism. Postganglionic branches of the splanchnic nerve innervate the liver and fat deposits of the abdomen. Activation of the splanchnic nerve can result in fat metabolism and the liberation of fatty acids, as well as glycogen breakdown and the release of glucose from the liver. Fat metabolism coupled with increased energy expenditure may result in a net reduction in fat reserves.

Figure 9:
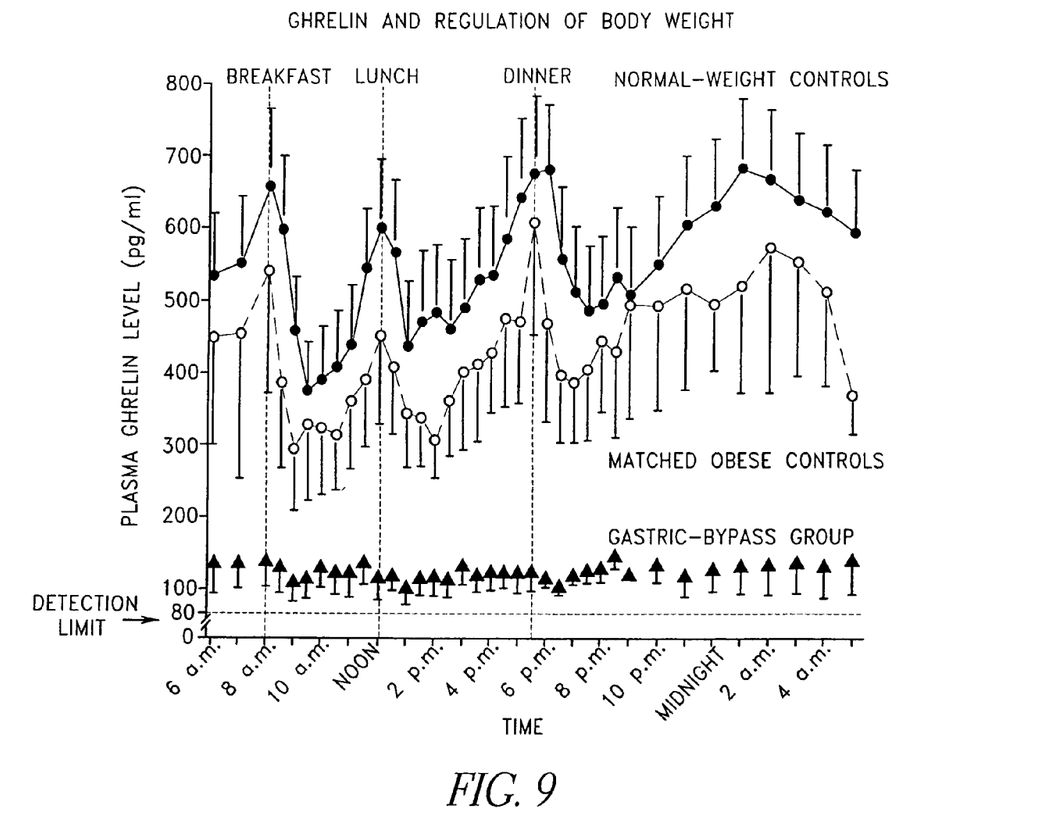
FIG. 9 is a graph of known plasma ghrelin levels over a daily cycle, for various subjects.

It may also be desirable to titrate obesity therapy to plasma ghrelin levels. In humans, venous blood ghrelin levels range from approximately 250 pg/ml to greater than 700 pg/ml as shown in FIG. 9. Ghrelin levels rise and fall during the day with peak levels typically occurring just before meals. In patients with gastric bypass surgery, an effective treatment for obesity, ghrelin levels are more static and typically stay in a low range of 100 to 200 pg/ml. Splanchnic nerve activation, in the treatment of obesity, could be titrated to keep ghrelin levels in the low range below 250 to 300 pg/ml. Reductions in food intake comparable to the increases in energy expenditure (i.e. 100 to 250 kcal/day), could yield a total daily kcal reduction of 200 to 500 per day, and 20 to 50 pounds of weight loss per year.

In anesthetized animals, electrical activation of the splanchnic nerve has also been shown to decrease insulin secretion. In obesity, insulin levels are often elevated, and insulin resistant diabetes (Type II) is common. Down-regulation of insulin secretion by splanchnic nerve activation may help correct insulin resistant diabetes.

Electrical activation of the splanchnic nerve can cause an increase in mean arterial blood pressure (MAP) above a baseline value. A drop in MAP below the baseline can follow this increase. Because a sustained increase in MAP is undesirable, the stimulation pattern can be designed to prevent an increase in MAP. One strategy would be to have a relatively short signal-on time followed by a signal-off time of an equal or longer period. This would allow the MAP to drop back to or below the baseline. The subsequent signal-on time would then raise the MAP, but it may start from a lower baseline. In this manner a sinusoidal-like profile of the MAP could be set up during therapy delivery that would keep the average MAP within safe limits. The rise in MAP is accompanied by a decrease in heart rate which is a compensatory mechanism that may also normalize MAP with sustained stimulation for more than approximately 10 minutes.

Alternatively, an alpha-sympathetic receptor blocker, such a prazosin could be used to blunt the rise in MAP. Alpha-blockers are commonly available antihypertensive medications. The rise in MAP seen with splanchnic nerve stimulation is the result of alpha-receptor activation, which mediates arterial constriction. Because the affects of this therapy on reduced food intake and energy expenditure are related to beta-sympathetic receptor activity, addition of the alpha-blocker would not likely alter the therapeutic weight loss benefits.

Figure 10:
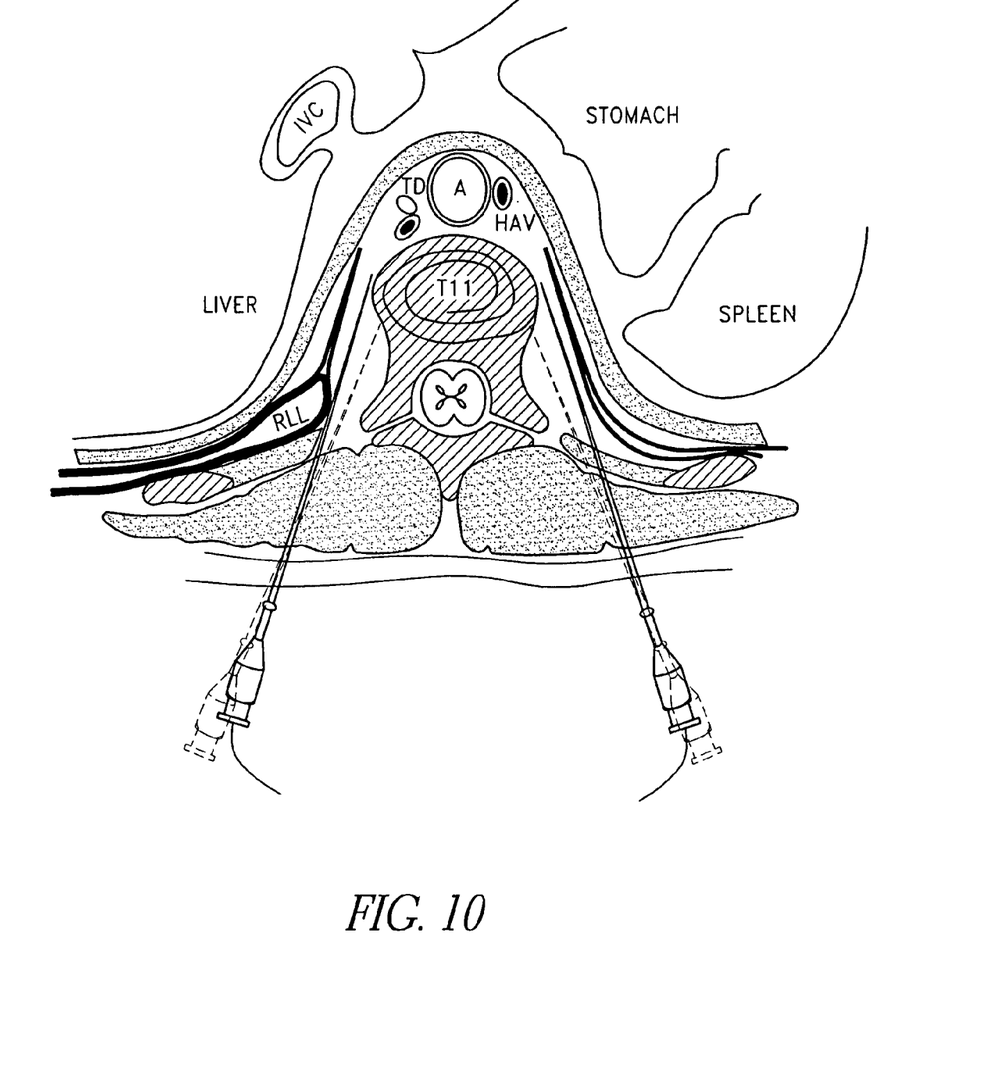
FIG. 10 is a section view of an exemplary instrument placement which can be used in the method of the present invention, for implantation of an electrode assembly.

Implantation of the lead/electrode assembly for activation of the greater splanchnic nerve is ideally accomplished percutaneously using an introducer as shown in FIG. 10. The introducer could be a hollow needle-like device that would be placed posteriorly through the skin between the ribs paramidline at the T9-T12 level of the thoracic spinal column. A posterior placement with the patient prone is preferred to allow bilateral electrode placement at the splanchnic nerves, if required. Placement of the needle could be guided using fluoroscopy, ultrasound, or CT scanning. Proximity to the splanchnic nerve by the introducer could be sensed by providing energy pulses to the introducer to electrically activate the nerve while monitoring for a rise in MAP. All but the very tip of the introducer would be electrically isolated so as to focus the energy delivered to the tip of the introducer. The lower the current amplitude required to cause a rise in the MAP, the closer the introducer tip would be to the nerve. Ideally, the introducer tip serves as the cathode for stimulation. Alternatively, a stimulation endoscope could be placed into the stomach of the patient for electrical stimulation of the stomach. The evoked potentials created in the stomach could be sensed in the splanchnic nerve by the introducer. To avoid damage to the spinal nerves, the introducer could sense evoked potentials created by electrically activating peripheral sensory nerves. Once the introducer was in proximity to the nerve, a catheter type lead electrode assembly would be inserted through the introducer and adjacent to the nerve. Stimulating the nerve and monitoring for a rise in MAP could be used to confirm electrode placement. The lead and the IPG would be implanted subcutaneously in the patient's back or side. The lead would be appropriately secured to avoid dislodgement. The lesser and least splanchnic nerves may also be activated to some degree by lead/electrode placement according to the above procedure, due to their proximity to the splanchnic nerve.

Percutaneous placement of the lead electrode assembly could be enhanced using direct or video assisted visualization. An optical port could be incorporated into the introducer.

A separate channel would allow the electrode lead assembly to be inserted and positioned, once the nerve was visualized. Alternatively, a percutaneous endoscope could be inserted into the chest cavity for viewing advancement of the introducer to the nerve. The parietal lung pleuron is relatively clear, and the nerves and introducer can be seen running along the vertebral bodies. With the patient prone, the lungs are pulled forward by gravity creating a space for the endoscope and for viewing. This may avoid the need for single lung ventilation. If necessary, one lung could be collapsed to provide space for viewing. This is a common and safe procedure performed using a bifurcated endotracheal tube. The endoscope could also be placed laterally, and positive $CO_2$ pressure could be used to push down the diaphragm, thereby creating a space for viewing and avoiding lung collapse.

Alternatively, stimulation electrodes could be placed along the sympathetic chain ganglia from approximately vertebra T4 to T11. This implantation could be accomplished in a similar percutaneous manner as above. This would create a more general activation of the sympathetic nervous system, though it would include activation of the neurons that comprise the splanchnic nerves.

Alternatively, the lead/electrode assembly could be placed intra-abdominally on the portion of the splanchnic nerve that resides retroperitoneally on the abdominal aorta just prior to synapsing in the celiac ganglia. Access to the nerve in this region could be accomplished laparoscopically, using typical laparoscopic techniques, or via open laparotomy. A cuff electrode could be used to encircle the nerve unilaterally or bilaterally. The lead could be anchored to the crus of the diaphragm. A cuff or patch electrode could also be attached to the celiac ganglia unilaterally or bilaterally. Similar activation of the splanchnic branches of the sympathetic nervous system would occur as implanting the lead electrode assembly in the thoracic region.

An alternative lead/electrode placement would be a transvascular approach. Due to the proximity of the splanchnic nerves to the azygous veins shown in FIG. 10, and in particular the right splanchnic nerve and right azygous vein, modulation could be accomplished by positioning a lead/electrode assembly in this vessel. Access to the venous system and azygous vein could occur via the subclavian vein using standard techniques. The electrode/lead assembly could be mounted on a catheter. A guidewire could be used to position the catheter in the azygous vein. The lead/electrode assembly would include an expandable member, such as a stent. The electrodes would be attached to the stent, and using balloon dilation of the expandable member, could be pressed against the vessel wall so that energy delivery could be transferred to the nerve. The expandable member would allow fixation of the electrode lead assembly in the vessel. The IPG and remaining lead outside of the vasculature would be implanted subcutaneously in a manner similar to a heart pacemaker.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

What is claimed is:

1. A method for treating obesity, comprising:
   monitoring a patient parameter; and
   electrically activating a splanchnic nerve in said patient so as to achieve a desired change in said monitored parameter;
   wherein the splanchnic nerve is selected from the group consisting of the greater splanchnic nerve, the lesser splanchnic nerve, and the least splanchnic nerve;
   wherein said monitored parameter comprises an arterial blood pressure; and
   wherein said electrically activating comprises activating the sympathetic nervous system with stimulation parameters that keep the arterial blood pressure within safe limits.

2. A method for treating a medical disorder, comprising:
   monitoring a vital sign and a second parameter in a patient; and
   electrically activating the sympathetic nervous system of said patient so as to achieve a desired change in said second parameter;
   wherein said medical disorder being treated comprises obesity;
   said vital sign comprises an arterial blood pressure;
   said second parameter comprises a plasma catecholamine level;
   said electrically activating comprises activating the splanchnic nerve to achieve an increased plasma catecholamine level; and
   said electrical activation has a signal-on time no greater than a signal-off time.

* * * * *